(12) United States Patent
Liu et al.

(10) Patent No.: US 11,730,870 B2
(45) Date of Patent: Aug. 22, 2023

(54) INTEGRATED MEMBRANE OXYGENATORS

(71) Applicant: JIANGSU STMED TECHNOLOGY CO., LTD., Jiangsu (CN)

(72) Inventors: Ridong Liu, Suzhou (CN); Peng Liu, Suzhou (CN); Yujie Liu, Suzhou (CN)

(73) Assignee: JIANGSU STMED TECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 18/056,257

(22) Filed: Nov. 17, 2022

(65) Prior Publication Data

US 2023/0075597 A1   Mar. 9, 2023

Related U.S. Application Data

(63) Continuation of application No. PCT/CN2021/124834, filed on Oct. 20, 2021.

(30) Foreign Application Priority Data

Jul. 14, 2021   (CN) .......................... 202110795391.0

(51) Int. Cl.
  *A61M 1/16*   (2006.01)
  *A61M 1/36*   (2006.01)
(52) U.S. Cl.
  CPC ........ *A61M 1/1629* (2014.02); *A61M 1/3666* (2013.01)
(58) Field of Classification Search
  CPC .... A61M 1/1563; A61M 1/16; A61M 1/1621; A61M 1/1629; A61M 1/1631;
(Continued)

(56) References Cited

U.S. PATENT DOCUMENTS 5,270,004 A * 12/1993 Cosentino ........... A61M 1/1629
                                                  422/46
5,762,868 A *  6/1998 Leonard .............. A61M 1/3623
                                                  604/6.14

(Continued)

FOREIGN PATENT DOCUMENTS

CN    201978219 U    9/2011
CN    104984427 A   10/2015
(Continued)

OTHER PUBLICATIONS

First Office Action in Chinese Application No. 202110795391.0 dated Dec. 3, 2021, 16 pages.

(Continued)

*Primary Examiner* — Benjamin J Klein
(74) *Attorney, Agent, or Firm* — Metis IP LLC

(57) ABSTRACT

The present disclosure discloses an integrated membrane oxygenator including an oxygenator and a filter attached to the oxygenator. The oxygenator may include an upper cover, a lower cover, a shell, and an oxygenation structure. Two ends of the filter may be respectively connected with the upper cover and the lower cover. The oxygenation structure may include a mandrel, an oxygen pressure membrane, and a temperature-changing membrane arranged inside the shell. The filter may include a filter shell, a diversion structure, and a filter screen arranged inside the filter shell. An inlet of the filter shell may be connected with a blood outlet on the lower cover of the oxygenator, and blood oxygenated by the oxygenator may directly enter the filter for filtration.

11 Claims, 8 Drawing Sheets

(58) Field of Classification Search
CPC .............. A61M 1/1698; A61M 1/3621; A61M 1/3627; A61M 1/369; A61M 2202/0413; A61M 2205/75

See application file for complete search history.

(56) References Cited

U.S. PATENT DOCUMENTS

| | | | | |
|---|---|---|---|---|
| 5,817,279 | A | * 10/1998 | Eilers | A61M 1/1698 422/46 |
| 5,823,987 | A | * 10/1998 | Elgas | A61M 1/1629 604/6.14 |
| 6,682,698 | B2 | * 1/2004 | Chambers | A61M 1/1678 604/6.14 |
| 8,388,566 | B2 | * 3/2013 | Reggiani | A61M 1/322 604/4.01 |
| 2009/0137939 | A1 | 5/2009 | Maianti et al. | |
| 2011/0268608 | A1 | 11/2011 | Reggiani et al. | |
| 2012/0193289 | A1 | * 8/2012 | Cloutier | A61M 1/1698 422/46 |
| 2013/0209314 | A1 | * 8/2013 | Roller | A61M 1/1698 422/46 |
| 2016/0296685 | A1 | * 10/2016 | Wu | A61M 1/1629 |
| 2017/0072123 | A1 | 3/2017 | Reggiani | |
| 2017/0128621 | A1 | 5/2017 | Sasaki | |
| 2020/0206404 | A1 | * 7/2020 | Wu | A61M 1/1698 |

FOREIGN PATENT DOCUMENTS

| | | | | |
|---|---|---|---|---|
| CN | 105555333 | A | 5/2016 | |
| CN | 105828848 | A | 8/2016 | |
| CN | 105833373 | A | 8/2016 | |
| CN | 106029118 | A | 10/2016 | |
| CN | 106573096 | A | 4/2017 | |
| CN | 109224163 | A | 1/2019 | |
| CN | 208893292 | U * | 5/2019 | .......... A61M 1/1621 |
| CN | 109224163 | B * | 6/2019 | .......... A61M 1/1623 |
| CN | 209475259 | U | 10/2019 | |
| CN | 209475259 | U * | 10/2019 | .......... A61M 1/1623 |
| WO | WO-2021042358 | A1 * | 3/2021 | |

OTHER PUBLICATIONS

Decision to Granta Patent in Chinese Application No. 202110795391.0 dated Apr. 18, 2022, 7 pages.

* cited by examiner

INTEGRATED MEMBRANE OXYGENATORS

CROSS-REFERENCE TO RELATED APPLICATIONS

This application is a continuation of International Patent Application No. PCT/CN 2021/124834, filed on Oct. 20, 2021, which claims priority to Chinese Patent Application No. 202110795391.0, filed on Jul. 14, 2021, the entire contents of each of which are hereby incorporated by reference.

TECHNICAL FIELD

The present disclosure relates to the technical field of medical devices, and in particular, to integrated membrane oxygenators.

BACKGROUND

A membrane oxygenator is a medical device that replaces a lung in case of cardiac arrest, which has a function of regulating content of oxygen and carbon dioxide in blood. The membrane oxygenator is an essential medical device for cardiovascular surgery and also an essential medical device for the treatment of acute respiratory disease and the stage of waiting for lung transplantation.

An oxygenator and a filter may need to be used at the same time during extracorporal circulation. The oxygenator may be configured to perform gas exchange on blood to maintain oxygen supply of a patient. The filter may be configured to filter an embolus (a bubble or a solid particle) in the blood, which may be the last safety barrier for blood to be returned to the body. A hose connection may often be used between the oxygenator and the filter. However, this way may increase the workload of a doctor before clinical use, a possibility of product contamination, and the contact area between blood and a non-self system, resulting in increased blood damage and increased damage to blood flowing through the connection point since a connection point is not a smooth transition.

Therefore, it is desirable to provide a membrane oxygenator with few installation steps that can reduce contaminants.

SUMMARY

The embodiments of the present disclosure provide an integrated membrane oxygenator including an oxygenator and a filter attached to the oxygenator. The oxygenator may include an upper cover, a lower cover, a shell, and an oxygenation structure. The upper cover may be divided into a first blood path space, a first gas path space, and a first water path space sequentially from a center to an outer edge. The upper cover may be provided with a gas inlet connected with the first gas path space, a first vent connected with the first blood path space, and a water inlet connected with the first water path space. The lower cover may be divided into a second blood path space, a second gas path space, and a second water path space sequentially from a center to an outer edge. The lower cover may be provided with a blood outlet connected with the second blood path space, a gas outlet connected with the second gas path space, and a water outlet connected with the second water path space. Two ends of the shell may be respectively connected with the upper cover and the lower cover. A blood inlet connected with an inner cavity of the shell may be arranged on the shell near the upper cover. The oxygenation structure arranged in the inner cavity of the shell may include a mandrel, an oxygen pressure membrane, and a temperature-changing membrane. An upper end of the mandrel may enter the first blood path space. The upper end of the mandrel is opposite to the first vent. A lower end of the mandrel may be opposite to the blood outlet. The oxygen pressure membrane may be arranged around the mandrel. The oxygen pressure membrane may be connected with the first gas path space and the second gas path space. The temperature-changing membrane may be arranged around the oxygen pressure membrane, and the temperature-changing membrane may be connected with the first water path space and the second water path space. The filter may include a filter shell, a diversion structure, and a filter screen. The diversion structure and the filter screen may be arranged in a cavity of the filter shell. A lower part of the filter shell may be provided with an outlet connected with the cavity of the filter shell. An upper part of the filter shell may be provided with an inlet connected with the cavity of filter shell. The inlet may be connected with the blood outlet. A top surface of the diversion structure may be provided with a protruding part that protrudes towards the inlet. The protruding part may be opposite to the lower end of the mandrel, and the filter screen may be located between a bottom surface of the filter shell and the diversion structure.

In some embodiments, the diversion structure may include a core and a diversion cover. The diversion cover may be arranged on the core. The filter screen may be arranged on an outer periphery of the core and located between an bottom surface of the filter shell and the diversion cover, and an upper end of the diversion cover may be the protruding part. A first channel may be arranged between the diversion cover and the filter shell. A second channel may be arranged between the filter screen and the filter shell, and the first channel may be connected with the second channel. An accommodating space may be formed among the core, the filter screen, and the bottom surface of the filter shell, and the accommodating space may be connected with the outlet.

In some embodiments, the diversion cover may include a first opening, a second opening, and a transitional surface extending from the first opening to the second opening. The first opening may be smaller than the second opening. The first opening may be below the mandrel, and a unidirectional membrane may be arranged at the first opening. A lower part of the core may be cylindrical, and an upper part of the core may be tightened from an edge to a middle part. The upper part of the core passing through the second opening may be located below the first opening. A side of the core may be connected with the diversion cover. A third channel may be arranged between the upper part of the core and an inner side of the diversion cover, and the third channel may be connected with the accommodating space.

In some embodiments, the bottom surface of the filter shell may have a protrusion arranged along an inner wall of the filter shell. A lower end of the filter screen may be connected with the protrusion, and an upper end of the filter screen may be connected with the diversion cover.

In some embodiments, a gap may be arranged between the temperature-changing membrane and an inner wall of the shell, and a width of the gap may gradually decrease from the upper cover to the lower cover.

In some embodiments, the oxygenator may further include a first plugging layer and a second plugging layer. The first plugging layer may be arranged at a junction of the shell and the upper cover, and the second plugging layer may be arranged at a junction of the shell and the lower cover. The oxygen pressure membrane may include a plurality of ventilation pipes, and each ventilation pipe of the plurality of ventilation pipes may be a hollow pipe with openings at both ends. One end of each ventilation pipe may penetrate into the first plugging layer and may be connected with the first gas path space, and the other end of each ventilation pipe may penetrate into the second plugging layer and may be connected with the second gas path space. The temperature-changing membrane may include a plurality of temperature-changing pipes, and each temperature-changing pipe of the plurality of temperature-changing pipes may be a hollow pipe with openings at both ends. One end of each temperature-changing pipe may penetrate into the first plugging layer and may be connected with the first water path space, and the other end of each temperature-changing pipe may penetrate into the second plugging layer and may be connected with the second water path space.

In some embodiments, the integrated membrane oxygenator may further include a turbulence structure for guiding blood to flow transversely, and the turbulence structure may be arranged between the shell and the temperature-changing membrane.

In some embodiments, the turbulence structure may include a plurality of protrusions protruding from the inner wall of the shell towards the temperature-changing membrane. The plurality of protrusions may be distributed in a ladder shape, and a distance between the protrusion close to the upper cover and the temperature-changing membrane may be greater than a distance between the protrusion close to the lower cover and the temperature-changing membrane.

In some embodiments, the upper cover may be further provided with a recirculation port connected with a first vent, and the shell may be provided with a second vent. The second vent may be provided with a unidirectional breathable membrane.

In some embodiments, the shell may be a cylindrical shell, and an inner diameter of the shell may decrease sequentially from the upper cover to the lower cover. A cross section of the mandrel may gradually decrease from the upper cover to the lower cover.

In some embodiments, the upper cover may be provided with a first partition ring and a second partition ring. The second partition ring may be arranged around the first partition ring. The first partition ring may partition the first blood path space and the first gas path space, and the second partition ring may partition the first gas path space and the first water path space.

The lower cover may be provided with a third partition ring and a fourth partition ring. The fourth partition ring may be arranged around the third partition ring. The third partition ring may partition the second blood path space and the second gas path space, and the fourth partition ring may partition the second gas path space and the second water path space.

BRIEF DESCRIPTION OF THE DRAWINGS

The present disclosure is further illustrated in terms of exemplary embodiments. These exemplary embodiments are described in detail with reference to the drawings. These embodiments are non-limiting exemplary embodiments, in which like reference numerals represent similar structures, and wherein.

DETAILED DESCRIPTION

In order to make the above objects, features and advantages of the present disclosure more clearly understood, combined with the drawings, detailed descriptions is made on the specific embodiments of the present disclosure below. In the following descriptions, many specific details are set forth to provide a thorough understanding of the present disclosure. However, the present disclosure may be implemented in many other ways different from those described herein. Those skilled in the art may make similar improvements without departing from the connotation of the present disclosure. Therefore, the present disclosure is not limited by the specific embodiments disclosed below.

It should be noted that when a component is referred to as being "fixed to" another component, it may be directly on the another element or there may be an intervening component. When a component is considered to be "connected with" another component, it may be directly connected with the another component or there may be an intervening component. Terms "vertical," "horizontal," "left," "right," and similar expressions used herein are merely for the purpose of illustration.

Unless otherwise defined, all technical and scientific terms used herein have the same meaning as commonly understood by those skilled in the art to which the present disclosure belongs. The terms used herein in the descriptions of the present disclosure are merely for the purpose of describing specific embodiments, which are not intended to limit the present disclosure. As used herein, the term "and/or" includes any and all combinations of one or more associated listed items.

Embodiments of the present disclosure provide an integrated membrane oxygenator including an oxygenator and a filter attached to the oxygenator. The oxygenator may be connected with the filter as a whole. Blood oxygenated by the oxygenator may directly enter the filter for filtration, thereby reducing a contact area between the blood and a non-self system, reducing blood damage, and avoiding a contamination risk brought due to a manual connection between the filter and the oxygenator.

Figure 1:
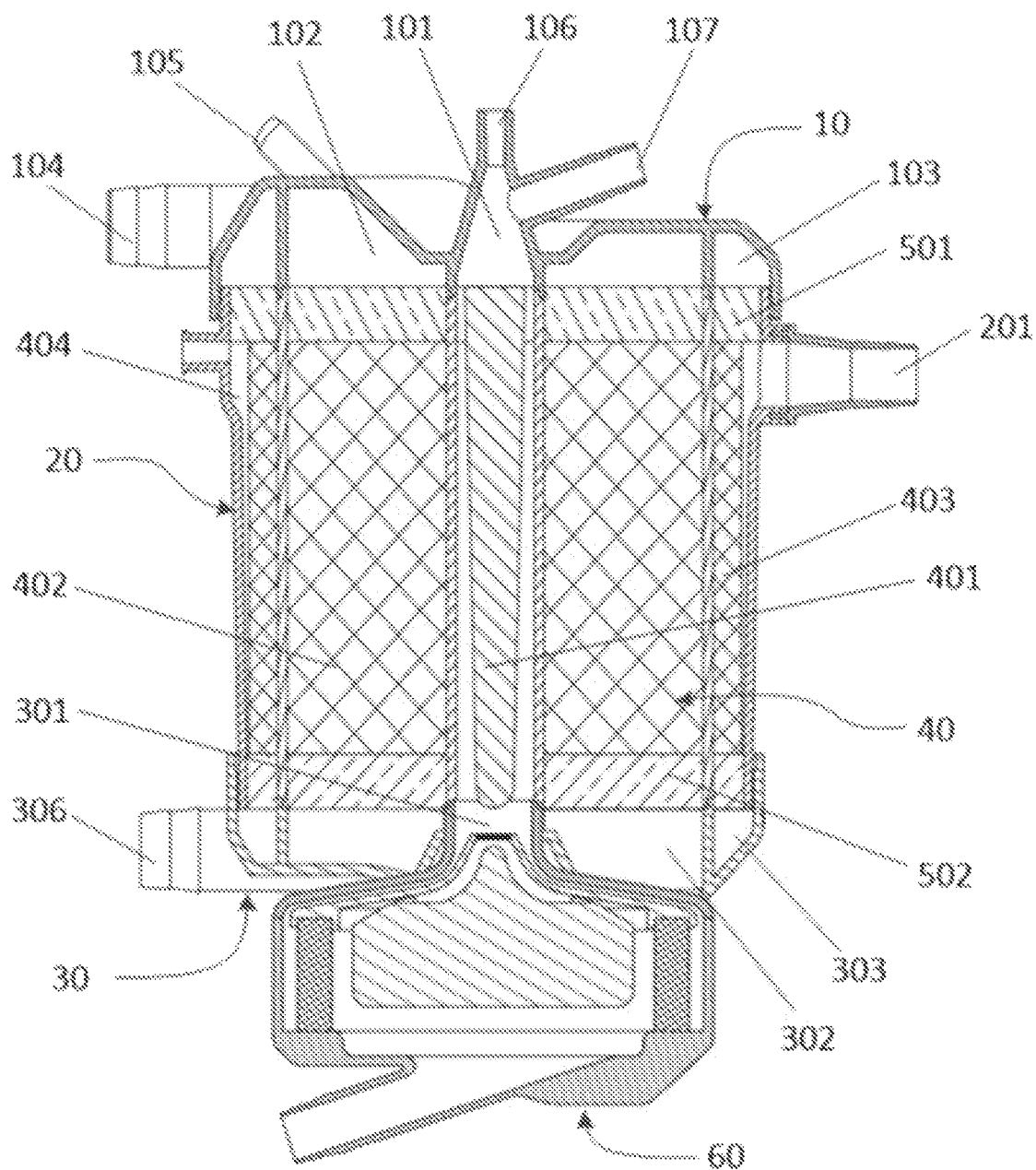
FIG. 1 is a schematic structural diagram of an integrated membrane oxygenator according to some embodiments of the present disclosure.

FIG. 1 is a schematic structural diagram of an integrated membrane oxygenator according to some embodiments of the present disclosure. As shown in FIG. 1, the oxygenator may include an upper cover 10, a lower cover 30, a shell 20, and an oxygenation structure 40. Two ends of the shell 20 may be respectively connected with the upper cover 10 and the lower cover 30. The oxygenation structure 40 may be arranged inside the shell 20. The oxygenation structure 40 may be configured to convert venous blood into arterial blood.

The upper cover may refer to an upper end structure of the oxygenator. In some embodiments, the upper cover 10 may be divided into a first blood path space 101, a first gas path space 102, and a first water path space 103 sequentially from a center to an outer edge. The upper cover 10 may be further provided with a gas inlet 105 connected with the first gas path space 102 and a water inlet 104 connected with the first water path space 103. The first blood path space 101 may be a cavity configured to accommodate partially oxygenated blood. The first gas path space 102 may be a cavity configured to accommodate gas. The first water path space 103 may be a cavity configured to accommodate water flowing into a temperature-changing water tank. In some embodiments, the upper cover 10 may include an upper cover body, a first partition ring, and a second partition ring. The upper cover body may have an opening and a bottom opposite to the opening, and the bottom may protrude away from the opening, so that a middle part of the upper cover body may be concave. The first partition ring may be arranged in the upper cover body.

The first partition ring may divide the concave space of the upper cover body into an inner space and an outer space. The space inside the first partition ring may be the first blood path space 101. The second partition ring may be arranged around the first partition ring. The second partition ring may divide the space outside the first partition ring into an inner space and an outer space. The space between the first partition ring and the second partition ring may be the first gas path space 102. The space between the second partition ring and an edge of the upper cover body may be the first water path space 103. The gas inlet 105 and the water inlet 104 may be both arranged in the upper cover body. The gas inlet 105 may be arranged between the first partition ring and the second partition ring. The water inlet 104 may be arranged between the second partition ring and the edge of the upper cover body.

The lower cover may refer to a lower end structure of the oxygenator. In some embodiments, the lower cover 30 may be divided into a second blood path space 301, a second gas path space 302, and a second water path space 303 sequentially from a center to an outer edge. The lower cover 30 may be provided with a blood outlet connected with the second blood path space 301, ana gas outlet (not shown in the figure) connected with the second gas path space 302, and a water outlet 306 connected with the second water path space 303. In a possible implementation, the lower cover 30 may include a lower cover body, a third partition ring, and a fourth partition ring. The lower cover body may have an opening and a bottom opposite to the opening, and the bottom may protrude away from the opening, so that a middle part of the lower cover body may be concave. The third partition ring may be arranged in the lower cover body. The third partition ring may divide the concave space of the lower cover body into an inner space and an outer space. The space inside the third partition ring may be the second blood path space 301. The fourth partition ring may be arranged around the third partition ring. The fourth partition ring may divide the space outside the third partition ring into an inner space and an outer space. The space between the third partition ring and the fourth partition ring may be the second gas path space 302. The space between the fourth partition ring and an edge of the lower cover body may be the second water path space 303. The blood outlet, the gas outlet, and the water outlet 306 may be all arranged in the upper cover body. The blood outlet may be arranged in the third partition ring. The gas outlet may be arranged between the third partition ring and the fourth partition ring. The water outlet 306 may be arranged between the fourth partition ring and the edge of the upper cover body.

The shell 20 may be configured to carry main components of the oxygenator. In some embodiments, two ends of the shell 20 may be respectively connected with the upper cover 10 and the lower cover 30. The blood inlet 201 connected with an inner cavity of the shell may be arranged on the shell 20 near the upper cover 10. In some embodiments, the shell 20 may be cylindrical. A first shell partition part and a second shell partition part may be arranged inside the shell 20. The first shell partition part and the second shell partition part may be annular parts. Two ends of the first shell partition part may be respectively connected with the first partition ring of the upper cover 10 and the third partition ring of the lower cover 30. Two ends of the second shell partition part may be respectively connected with the second partition ring of the upper cover 10 and the fourth partition ring of the lower cover 30.

The oxygenation structure 40 may be a main structure for achieving oxygenation, which is configured to perform oxygen and carbon dioxide exchange and convert venous blood into arterial blood. In some embodiments, the oxygenation structure 40 may be arranged in the inner cavity of the shell. The oxygenation structure 40 may include a mandrel 401, an oxygen pressure membrane 402, and a temperature-changing membrane 403. The mandrel 401 may be configured to converge and guide oxygenated blood. The oxygen pressure membrane may be a structure configured to perform oxygen and carbon dioxide exchange. The temperature-changing membrane may be configured for heat exchange with blood. An upper end of the mandrel 401 may enter the first blood path space 101. A lower end of the mandrel 401 may be opposite to the blood outlet. The oxygen pressure membrane 402 may be arranged around the mandrel 401. The oxygen pressure membrane 402 may be connected with the first gas path space 102 and the second gas path space 302. The temperature-changing membrane 403 may be arranged around the oxygen pressure membrane 402. The temperature-changing membrane 403 may be connected with the first water path space 103 and the second water path space 303. A gap 404 may be arranged between the temperature-changing membrane 403 and the shell 20, and a width of the gap 404 may gradually decrease from the upper cover 10 to the lower cover 30. Specifically, the mandrel 401 may be arranged in the first shell partition part. The oxygen pressure membrane 402 may be arranged between the first shell partition part and the second shell partition part. The temperature-changing membrane 403 may be arranged between an inner wall of the shell 20 and the second shell partition part. The temperature-changing membrane 403 may wrap an outer surface of the oxygen pressure membrane 402.

In some embodiments, after the upper cover 10, the shell 20, the lower cover 30, and the oxygenation structure 40 are assembled, in the upper cover 10, the first blood path space 101 may be not connected with the first gas path space 102, and the first gas path space 102 may be not connected with the first water path space 103. In the lower cover 30, the second blood path space 301 may be not connected with the second gas path space 302, and the second gas path space 302 may be not connected with the second water path space 303. Specifically, a first plugging layer 501 may be arranged at a junction of the upper cover 10 and the shell 20, and a second plugging layer 502 may be arranged at a junction of the lower cover 30 and the shell 20. The first plugging layer 501 may isolate the first blood path space 101, the first gas path space 102 and the first water path space 103, and may also isolate the inner cavity of the shell from each space of the upper cover 10. The second plugging layer 502 may isolate the second blood path space 301, the second gas path space 302, and the second water path space 303, and may also isolate the inner cavity of the shell from each space of the lower cover 30. In some embodiments, the first blood path space 101, the first gas path space 102, and the first water path space 103, and the inner cavity of the shell and each space of the upper cover 10 may be isolated through any other possible structure or manner. The second blood path space 301, the second gas path space 302, and the second water path space 303, and the inner cavity of the shell and each space of the lower cover 30 may be isolated through any other possible structure or manner.

The oxygenator may be a medical device that may replace a function of a person's lung for extra-corporeal gas exchange during surgery or life maintenance. The oxygenator may be composed of two functions, i.e., gas exchange and temperature control. In some embodiments, the gas exchange function may be implemented by the oxygen pressure membrane 402, and the temperature control function may be implemented by the temperature-changing membrane 403. In some embodiments, the oxygen pressure membrane 402 may include a plurality of ventilation pipes, each the ventilation pipe of the plurality of ventilation pipes may be a hollow pipe with openings at both ends, and an aperture size of the ventilation pipe may be within a range of 0.1 μm-5 μm. One end of each ventilation pipe may penetrate into the first plugging layer 501 and may be connected with the first gas path space 102, and the other end of each ventilation pipe may penetrate into the second plugging layer 502 and may be connected with the second gas path space 302. Pipe walls of at least part of the plurality of ventilation pipes may have micropores that merely allow gas to pass through and block red blood cells from passing through. In fact, the pipe wall of the ventilation pipe may also be regarded as a semipermeable membrane that merely allows gas to pass through. The oxygenator may achieve gas exchange process in blood through the semipermeable membrane. The temperature-changing membrane 403 may include a plurality of temperature-changing pipes, and each temperature-changing pipe of the plurality of temperature-changing pipes may be a hollow pipe with openings at both ends. One end of each temperature-changing pipe may penetrate into the first plugging layer 501 and may be connected with the first water path space 103, and the other end of each temperature-changing pipe may penetrate into the second plugging layer 502 and may be connected with the second water path space 303. In some embodiments, both the oxygen pressure membrane 402 and the temperature-changing membrane 403 may be composed of a large number of thin-walled hollow pipes. A difference may be that at least part of the hollow pipes used in the oxygen pressure membrane 402 are porous membranes for gas exchange with blood, and all the hollow pipes used in the temperature-changing membrane 403 are non-porous membrane for diversion and heat exchange with blood outside the hollow pipe.

Figure 2:
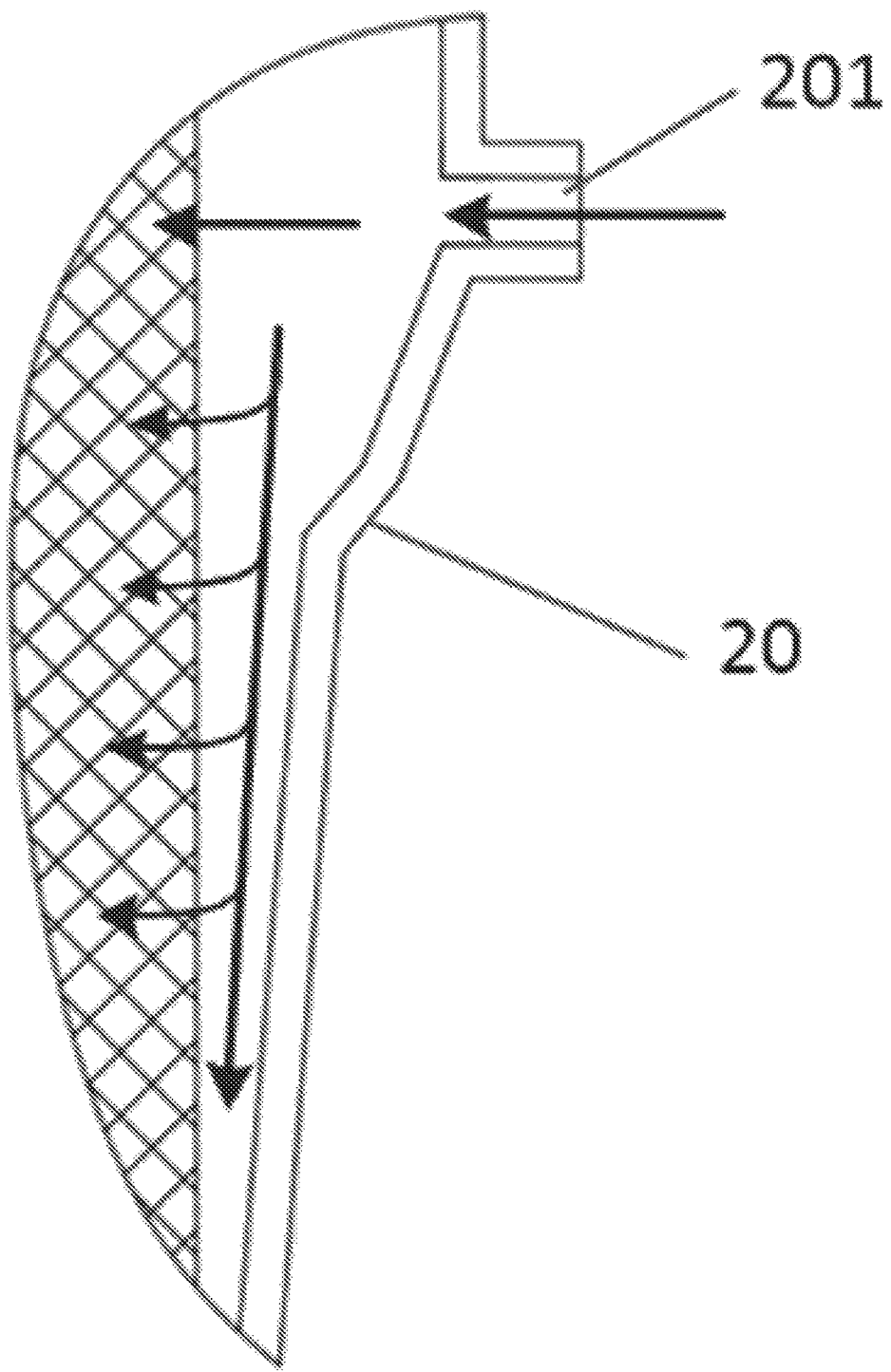
FIG. 2 is a partial schematic diagram of a structure of a shell according to some embodiments of the present disclosure.

FIG. 2 is a partial schematic diagram of a structure of a shell according to some embodiments of the present disclosure.

In some embodiments, a gap 404 may be arranged between the temperature-changing membrane 403 and an inner wall of the shell 20, a width of the gap 404 may gradually decrease from the upper cover 10 to the lower cover 30, and the blood inlet 201 may be close to the upper cover 10. In this way, when blood enters the oxygenator from the blood inlet 201, the gap 404 between the temperature-changing membrane 403 and an inner wall of the shell 20 may be filled. Because the gap 404 shows a wide-upper and narrow-lower shape (shown as FIG. 2), a small amount of blood may be filled with a lower part of the gap 404, and more blood may stay in an upper part of the gap 404. Driven by the blood continuously injected from the blood inlet 201, the blood that stays in the upper part of the gap 404 may continue to transversely pass through the temperature-changing membrane 403 and the oxygen pressure membrane 402, enter a space where the mandrel 401 is located, flow into the filter 60 connected with the space, and return to a human body after filtering.

In some embodiments, the specific manner in which the gap 404 between the temperature-changing membrane 403 and the shell 20 presents a gradually decreasing shape is not limited. In some embodiments, the shell 20 may be designed to be cylindrical, so that an inner diameter of the shell 20 may decrease sequentially from the upper cover 10 to the lower cover 30. In some embodiments, the temperature-changing pipes may be arranged to enable one end of the temperature-changing membrane 403 close to the lower cover 30 to be closer to the inner wall of the shell 20 than one end of the temperature-changing membrane 403 close to the upper cover 10. In other embodiments, the gap 404 between the temperature-changing membrane 403 and the shell 20 may present a gradually decreasing shape through a combination of the above two manners or any other possible structure or manner.

In some embodiments, the mandrel 401 may be designed to be a pyramid structure, so that a cross section of the mandrel 401 may be gradually decreased from the upper cover 10 to the lower cover 30 to achieve a better convergence of oxygenated blood.

In some embodiments, to enable more blood to transversely pass through the temperature-changing membrane and the oxygen pressure membrane for performing sufficient heat exchange and gas exchange, a turbulence structure may be also arranged between the shell and the temperature-changing membrane, which may guide the blood flow transversely.

Figure 3:
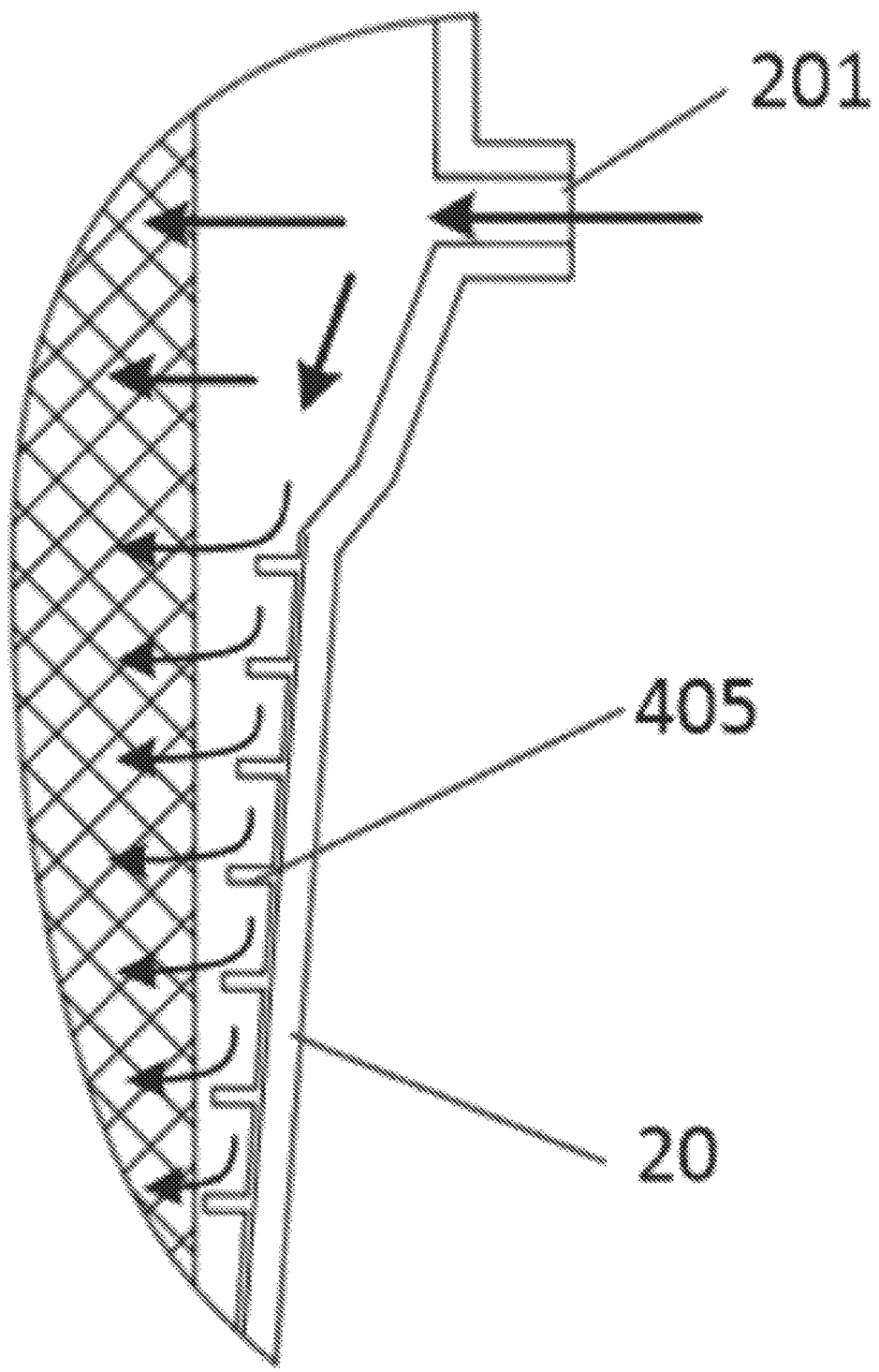
FIG. 3 is a partial schematic diagram of another structure of a shell according to some embodiments of the present disclosure.

FIG. 3 is a partial schematic diagram of another structure of a shell according to some embodiments of the present disclosure. As shown in FIG. 3, a turbulence structure may include a plurality of protrusions 405 protruding from an inner wall of the shell 20 towards the temperature-changing membrane 403. Blood may enter a gap between an inner wall of the shell 20 and the temperature-changing membrane 403 from the blood inlet 201. When flowing into the lower cover 30, the blood may be blocked by the protrusion 405, thereby forcing the blood to change the flow direction and enter the temperature-changing membrane 403 transversely. In some embodiments, the plurality of protrusions 405 constituting the turbulence structure may be distributed in a ladder shape, and a distance between the protrusion 405 close to the upper cover 10 and the temperature-changing membrane 403 may be greater than a distance between the protrusion 405 close to the lower cover 30 and the temperature-changing membrane 403. With this design, the blood flowing to the lower cover 30 may be blocked by the each protrusion 405, so that as much blood as possible may transversely pass through the temperature-changing membrane 403 and the oxygen pressure membrane 402.

A gas exchange capacity may be usually related to a surface area of the oxygen pressure membrane and an oxygen concentration of a gas source. In addition, the gas exchange capacity may be also directly related to setting of a blood flow route. Specifically, regardless of whether a gas route and a blood flow route are in an opposite direction or a same direction, the longer the gas route is, the worse the gas exchange capacity is, and the gas exchange capacity may approach 0 when the gas route reaches 2 meters. Therefore, the higher a proportion of the blood flow route transversely passing through the oxygen pressure membrane is, the better the oxygenator effect is. The integrated membrane oxygenator provided by the embodiments of the present disclosure may improve the proportion of blood transversely passing through the oxygen pressure membrane through the arrangement of the blood inlet and the blood outlet, the gap between the temperature-changing membrane and the inner wall of the shell, and the turbulence structure, thereby enhancing the oxygenation effect of the oxygenator and achieving a relatively large gas exchange capacity using a relatively small surface area of the oxygen pressure membrane.

The layout of the oxygenator provided by the embodiments of the present disclosure may have a relatively large blood flow buffer area, so that when blood enters the oxygenator, more blood may transversely pass through the temperature-changing membrane and the oxygen pressure membrane at a slower speed and a contact time between the blood and the temperature-changing membrane and the oxygen pressure membrane may be longer, thereby achieving a better temperature change efficiency and oxygenation effect. The above design may also make drag loss of the oxygenator smaller, thereby reducing blood damage caused by the drag.

The oxygenation structure in the membrane oxygenator may usually include a mandrel, the temperature-changing membrane, and the oxygenation membrane arranged from inside to outside. The blood inlet may be arranged at a lower part of the oxygenator, and the blood outlet may be arranged at an upper part of the oxygenator. The flow route of blood in the oxygenator may be: blood inlet→a space where the mandrel is located→temperature-changing membrane-→oxygen pressure membrane→blood outlet. Since the space of the mandrel is relatively small, if the blood cannot be well buffered when the blood flows near the mandrel, a turbulent flow may be easy to form to cause blood damage. The layout of the oxygenator provided by the embodiments of the present disclosure may have a relatively large blood flow buffer area, so that when blood enters the oxygenator, more blood may transversely pass through the temperature-changing membrane and the oxygen pressure membrane at a slower speed and a contact time between the blood and the temperature-changing membrane and the oxygen pressure membrane may be longer, thereby achieving a better temperature change efficiency and oxygenation effect. The above design may also make drag loss of the oxygenator smaller, thereby reducing blood damage caused by the drag.

In addition to the gas exchange capacity and the temperature change capacity, main indicators of the oxygenator may also include a bubble removal capacity. A clinician may need to perform an exhaust operation on the membrane oxygenator before using the membrane oxygenator. In some embodiments, the bubbles in the oxygenator may be easily exhausted by reasonably arranging vents of the oxygenator, and no complicated exhaust operation may be required. In a specific embodiment, the upper cover 10 may be provided with a first vent 106 connected with the first blood path space 101, and the first vent 106 may be opposite to an upper end of the mandrel 401. Compared with an oxygenator with vents arranged on a side of a shell (the vents are not at a highest point of the entire product, which is easy to cause bubbles to gather, so that a doctor needs to continuously change an angle of the oxygenator by holding the oxygenator to exhaust the bubbles through the vents.) and an oxygenator whose internal bubbles cannot be observed intuitively (an object is needed to gently knock a shell of the oxygenator to make the bubbles hidden inside the oxygenator enter a place where the bubbles can be observed through the shell), the blood flow route of the oxygenator in the present disclosure may be more likely to gather air in the oxygenator near the mandrel along the blood flow and the bubbles may be easier to be exhausted through the first vent on the top of the upper cover since the bubbles in the blood move upward. The bubbles may be easily exhausted without knocking or rotating the oxygenator, it may be intuitively observed whether there is any residual bubble inside the oxygenator through the transparent cover, and it may be determined whether the product or the overall route have a safety risk by observing gathering of the bubbles at the top during an operation, so that measures may be taken as soon as possible to avoid serious consequences.

In some embodiments, since the shell 20 is in the form of a cylinder, some bubbles may not enter a space near the mandrel 401, but gather on the upper part of the shell 20. In order to exhaust the bubbles, a second vent 202 may be arranged on the shell 20 near the upper cover 10. In some embodiments, a hose may be configured to connect the second vent 202 with other components for exhausting. In other embodiments, a unidirectional breathable membrane 203 may also be provided on the second vent 202.

Figure 4:
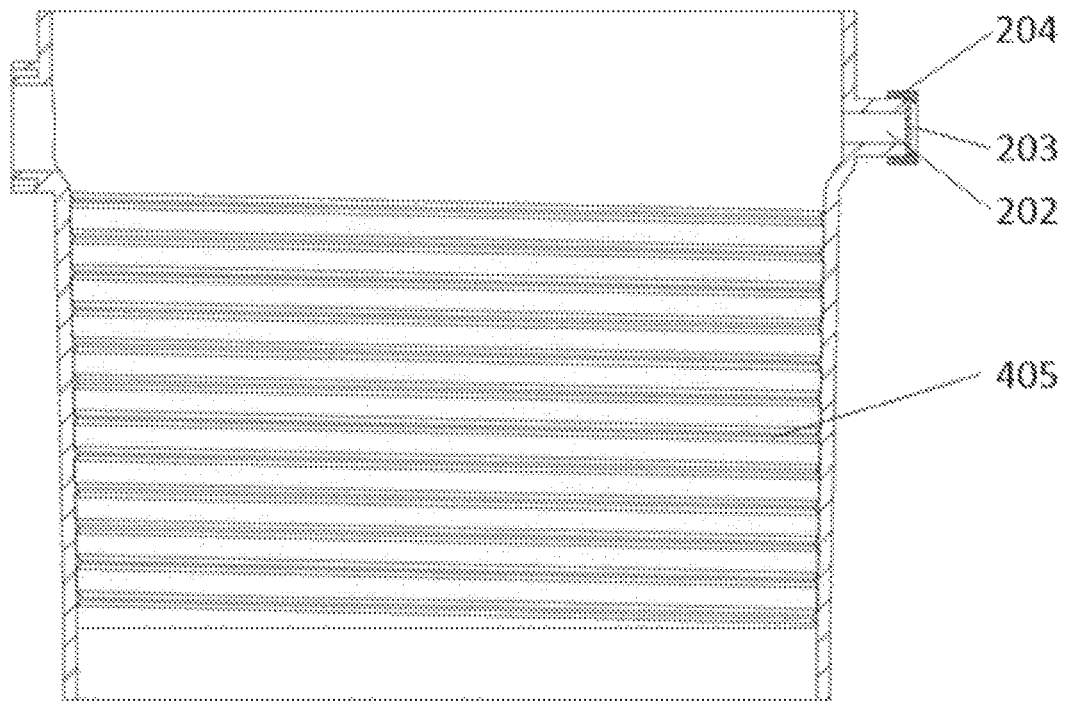
FIG. 4 is a schematic structural diagram of a shell provided with a second vent according to some embodiments of the present disclosure.

FIG. 4 is a schematic structural diagram of a shell provided with a second vent according to some embodiments of the present disclosure. As shown in FIG. 4, a compression cover 204 may be sheathed outside the unidirectional membrane, the compression cover 204 may be connected with the second vent 202 by threads or buckles to compress and fix the unidirectional breathable membrane 203. The unidirectional breathable membrane 203 may have micropores that merely allow gas to pass through but not allow the blood to pass through. Therefore, the second vent 202 provided with the unidirectional breathable membrane 203 may not need to be connected with other components to achieve a function of blocking blood and exhausting bubbles in the blood.

In some embodiments, the upper cover 10 may be further provided with a recirculation port 107 connected with the first vent 106. When oxygenated blood needs to be drawn for other purposes, the oxygenated blood near the mandrel may be drawn out by connecting the recirculation port.

Figure 5:
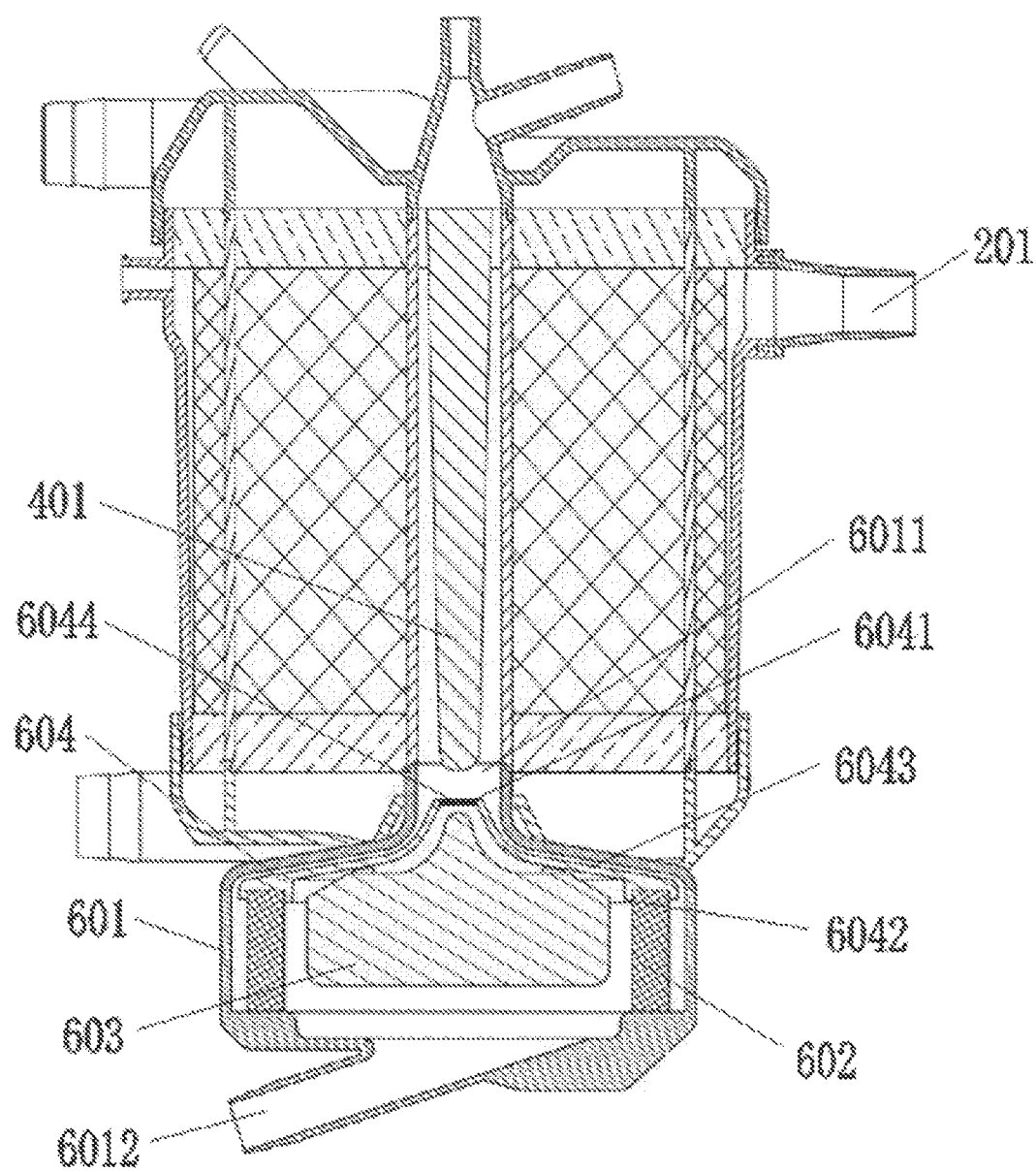
FIG. 5 is a schematic structural diagram of an integrated membrane oxygenator according to some embodiments of the present disclosure.

FIG. 5 is a schematic structural diagram of an integrated membrane oxygenator according to some embodiments of the present disclosure. As shown in FIG. 5, the filter 60 may include a filter shell 601, a filter screen 602, and a diversion structure. The diversion structure may be configured to disperse blood, so that the blood may slowly pass through the filter screen 602 to reduce damage to the blood. The pore diameter of the filter screen 602 may be less than 40 μm, which may filter a micro-embolus (including a large bubble, an gaseous microemboli, and a particle) above 40 μm to prevent the micro-embolus from blocking microcirculation and causing damage to an important organ. A structure of the filter 60 is described below.

A cavity may be arranged inside the filter shell 601, an upper part of the filter shell may be provided with an inlet 6011 connected with the cavity, a lower part of the filter shell may be provided with an outlet 6012 connected with the cavity, the inlet 6011 may be connected with a blood outlet or the second blood path space 301 of the oxygenator, and the inlet 6011 may be located below the mandrel of the oxygenator. Specifically, the filter shell may include a filter upper shell and a filter lower shell connected with the filter upper shell, a cavity may be formed between the filter upper shell and the filter lower shell, the inlet 6011 may be arranged on the filter upper shell, and the outlet 6012 may be arranged on the filter lower shell. In addition, a ring of protrusions may also be arranged along an inner wall of the filter shell on a bottom surface of the filter shell to install the filter screen, so as to form a blood flow channels on both sides of the filter screen, and the protrusions and the bottom surface of the filter shell may be integrally formed.

In some embodiments, the diversion structure may include a core 603 and a diversion cover 604. The core 603 may be configured to form dispersive blood flow channels. The diversion cover 604 may be configured to guide a flow direction of blood. The diversion cover 604 may be arranged on the core 603, the filter screen 602 may be arranged around the diversion structure, an upper end of the filter screen 602 may be connected with the diversion cover 604, and a lower end of the filter screen 602 may be connected with a bottom of the filter shell 601, and a structure of the filter screen 602 may be similar to be hollow cylindrical. A first channel may be arranged between the diversion cover 604 and the filter shell 601, a second channel may be arranged between the filter screen 602 and the filter shell 601, and the first channel may be connected with the second channel. An accommodation space may be formed among the core 603, the filter screen 602, and the bottom surface of the filter shell 601, and the accommodating space may be connected with the outlet.

In some embodiments, the diversion cover 604 may be trumpet-shaped, which may include a first opening 6041, a second opening 6042, and an arc-shaped transitional surface 6043 extending from the first opening 6041 to the second opening 6042, and the first opening 6041 may be smaller than the second opening 6042. A lower part of the core 603 may be cylindrical, for example, the core 603 may be a cylindrical shape adapted to a shape of the filter screen 602. An upper part of the core 603 may be tightened from an edge to a middle part, so that the core 603 may present a small-upper and large-lower shape. The upper part of the core 603 passing through the second opening 6042 may be located below the first opening, a side of the core 603 may be connected with the second opening 6042, a third channel may be arranged between the upper part of the core 603 and an inner side of the diversion cover 604, and the third channel may be connected with the accommodating space. A unidirectional membrane 6044 may be arranged at the first opening 6041, and the unidirectional membrane 6044 may allow the bubbles to enter the second blood path space 301 from a gap.

The upper end of the filter screen 602 may be connected with the diversion cover, and the lower end of the filter screen 602 may be connected with the protrusion on the bottom surface of the filter shell. The oxygenated blood may flow into the first channel of the filter from the blood outlet, flow into the second channel along the first channel, and then transversely pass through the filter screen 602 from the second channel, the filter screen 602 may block microbubbles and solid particles, the filtered blood may flow into the accommodation space, flow out from the outlet 6012 at the bottom of the filter shell, and the oxygenated blood may be returned to the human body through connecting pipes. If the blood passing through the filter screen 602 is mixed with bubbles, the bubbles in the blood may move upward, enter the third channel from the accommodation space, gather near the first opening 6041, enter the second blood path space 301 through the unidirectional membrane 6044, and continue to move upward until the bubbles are exhausted through the first vent 106. In this embodiment, after entering the filter, the blood may flow slowly in each channel of the filter and be in full contact with the filter screen, which may improve filtration efficiency. Moreover, when there are bubbles in the filtered blood, the bubbles may quickly reach the first opening 6041 along a narrow space of the third channel, which may accelerate a speed of exhausting the bubbles in the blood.

Due to different functions of the oxygenator and the filter, the oxygenator and the filter may be generally in the form of two independent devices, and be connected through a hose when used. When the blood flows through the connector, blood damage may be easy to be caused. In the embodiment of the present disclosure, the filter and the oxygenator may be integrated, the blood filtered by oxygenator may not need to flow through a long pipe for filtering, which can avoid damage to the blood caused by pipe connection. In some embodiments, the filter and the oxygenator may be connected and integrated by physical devices, which can also achieve function optimization as follows.

1. The filter may share the first vent with the oxygenator, if there are bubbles in the blood filtered by the filter screen, the bubbles may automatically enter the space where the mandrel is located, and then be exhausted from the first vent, and there is no need to install an extra vent on the filter.

2. The diversion structure may be designed to disperse and guide the blood, reduce the blood flow rate, make the blood fully contact with the filter screen, which can improve the filtration effect and reduce blood damage.

In some embodiments, the usage and working process of the integrated membrane oxygenator are as follows.

In the process of a surgery or maintaining life signs, the blood inlet 201 may be connected with a human vein through the hose, and the outlet 6012 of the filter may be connected with a human artery through the hose, and the water inlet 104 and the water outlet 306 may be respectively connected with the temperature-changing water tank through the hose. The gas inlet 105 may be connected with the gas source through the hose. The temperature-changing water tank may input water with a set temperature into the inner cavity of each temperature-changing pipe composing the temperature-changing membrane 403 through the water inlet 104, the gas source may input oxygen with a set concentration into the inner cavity of each ventilation pipe composing the oxygenation membrane through the gas inlet 105. When the venous blood enters the shell 20 through the blood inlet 201, the blood flowing through the temperature-changing membrane 403 may exchange heat with the blood through the outer wall of the temperature-changing pipe, so as to achieve a purpose of heating or cooling the blood. The venous blood that completes the temperature exchange may transversely pass through the oxygen pressure membrane 402, the gas may be inside the ventilation pipe and the blood may be outside the ventilation pipe. The gas and the blood may exchange oxygen and carbon dioxide through diffusion on both sides of the semipermeable membrane. At this time, the carbon dioxide in the venous blood may enter the inner cavity of the ventilation pipe, and the oxygen in the ventilation pipe may enter the blood. After the process of the venous blood being converted into the arterial blood is completed, the arterial blood may continue to enter the filter, flow through the first channel, the second channel, and the filter screen in sequence, gather in the accommodating space, and return to the human body through the outlet 6012 at the bottom of the filter shell to maintain oxygen supply to the patient. The role of the integrated membrane oxygenator is consistent with the human body's own lung function.

Figure 6:
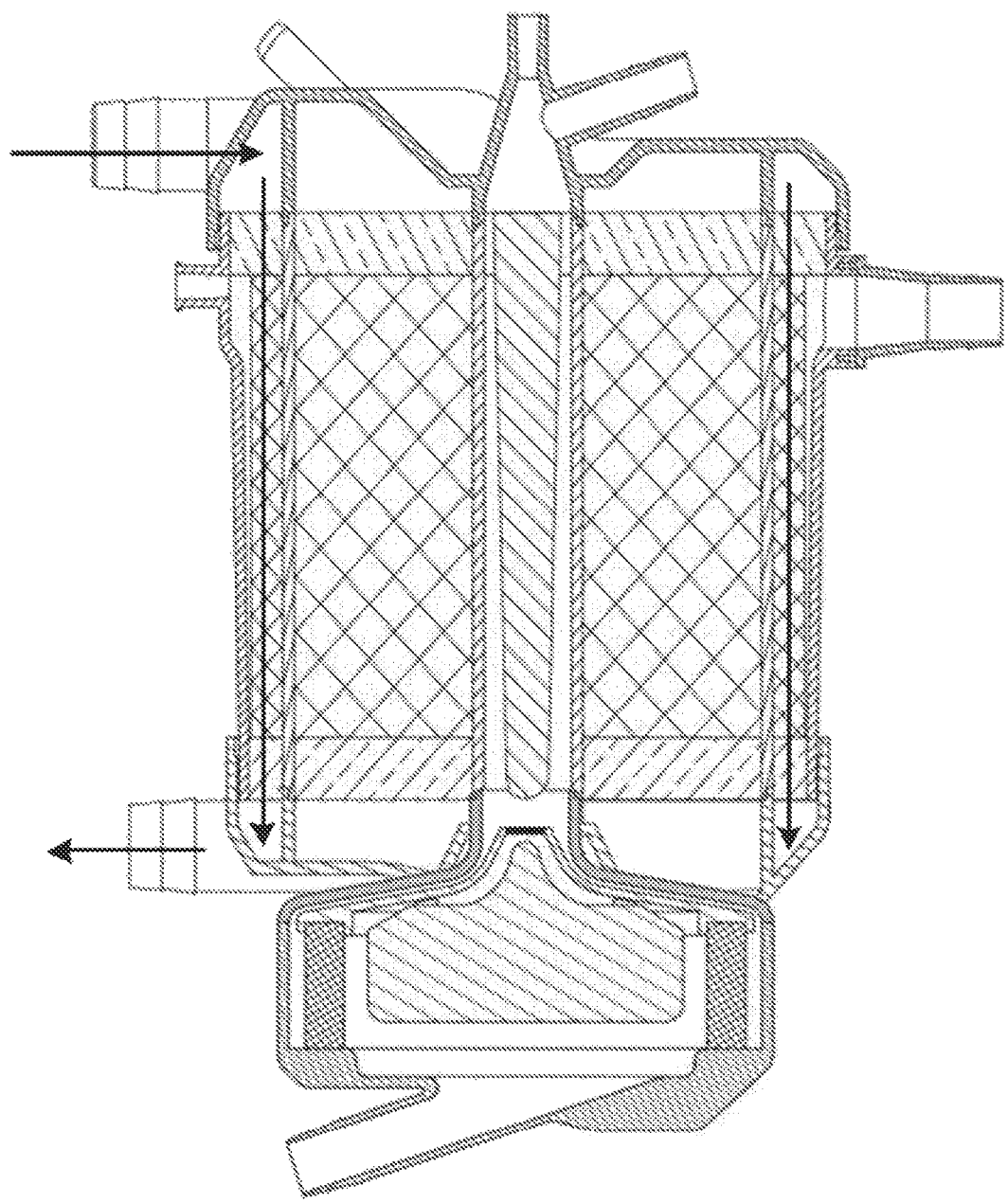
FIG. 6 is a schematic diagram of a flow direction of water in the oxygenator according to some embodiments of the present disclosure.

FIG. 6 is a schematic diagram of a flow direction of water in an integrated membrane oxygenator according to some embodiments of the present disclosure. As shown in FIG. 6, the water in the temperature-changing water tank may flow into the first water path space 103 from the water inlet 104, enter the second water path space 303 through the temperature-changing pipe, and then return to the temperature-changing water tank from the water outlet 306. When the blood flows through the temperature-changing pipe, the blood exchanges heat with the water in the variable temperature tube to adjust the blood temperature to the desired temperature range.

Figure 7:
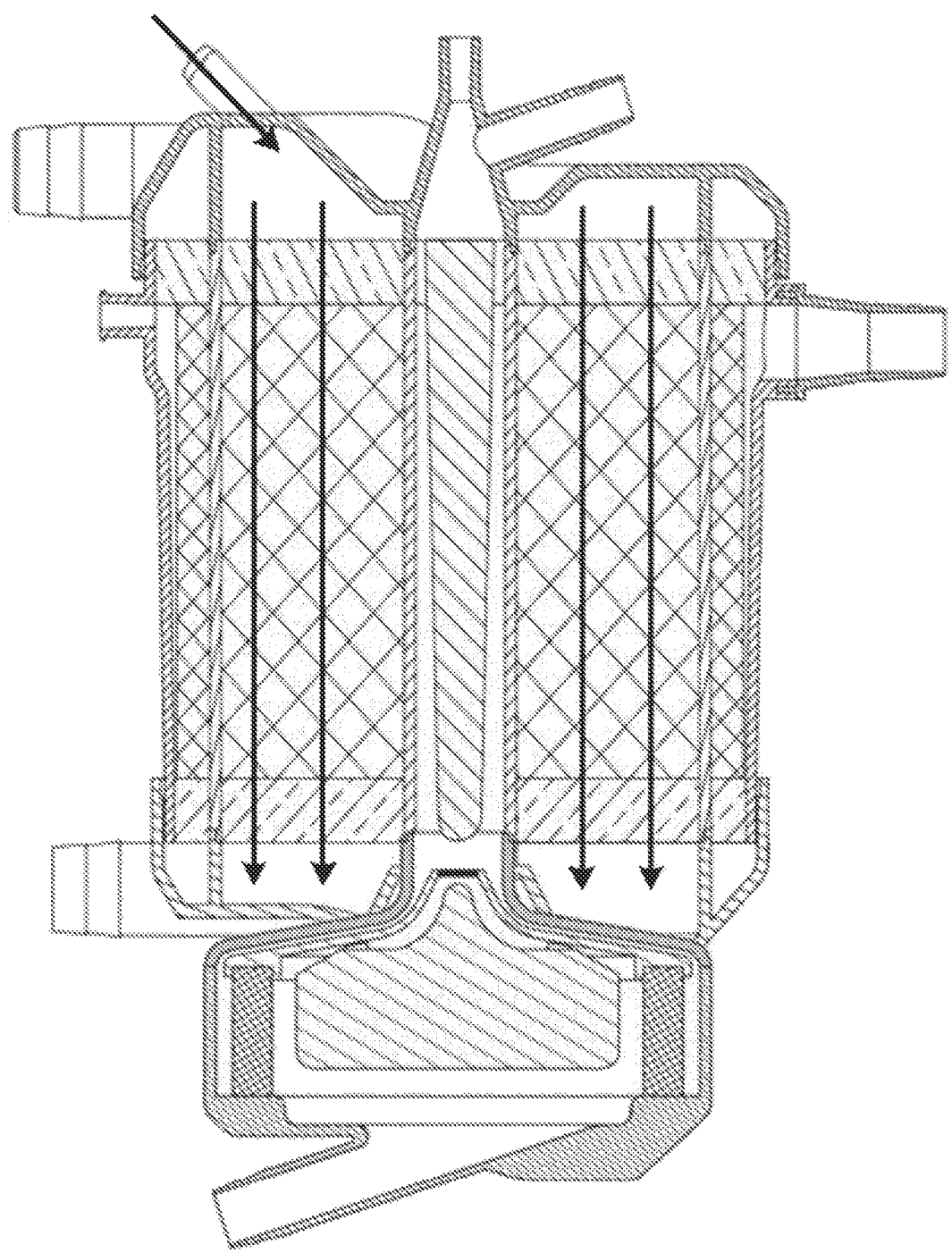
FIG. 7 is a schematic diagram of a flow direction of gas in the oxygenator according to some embodiments of the present disclosure.

FIG. 7 is a schematic diagram of a flow direction of gas in an integrated membrane oxygenator according to some embodiments of the present disclosure. As shown in FIG. 7, oxygen in a gas source may enter the first gas path space 102 from the gas inlet 105, and then flow into a ventilation pipe. Blood flowing through the ventilation pipe may exchange gas with the ventilation pipe, the oxygen in the ventilation pipe may combine with the blood, the carbon dioxide in the blood may enter the ventilation pipe, flow into the second gas path space 302, and be exhausted from the gas outlet.

Figure 8:
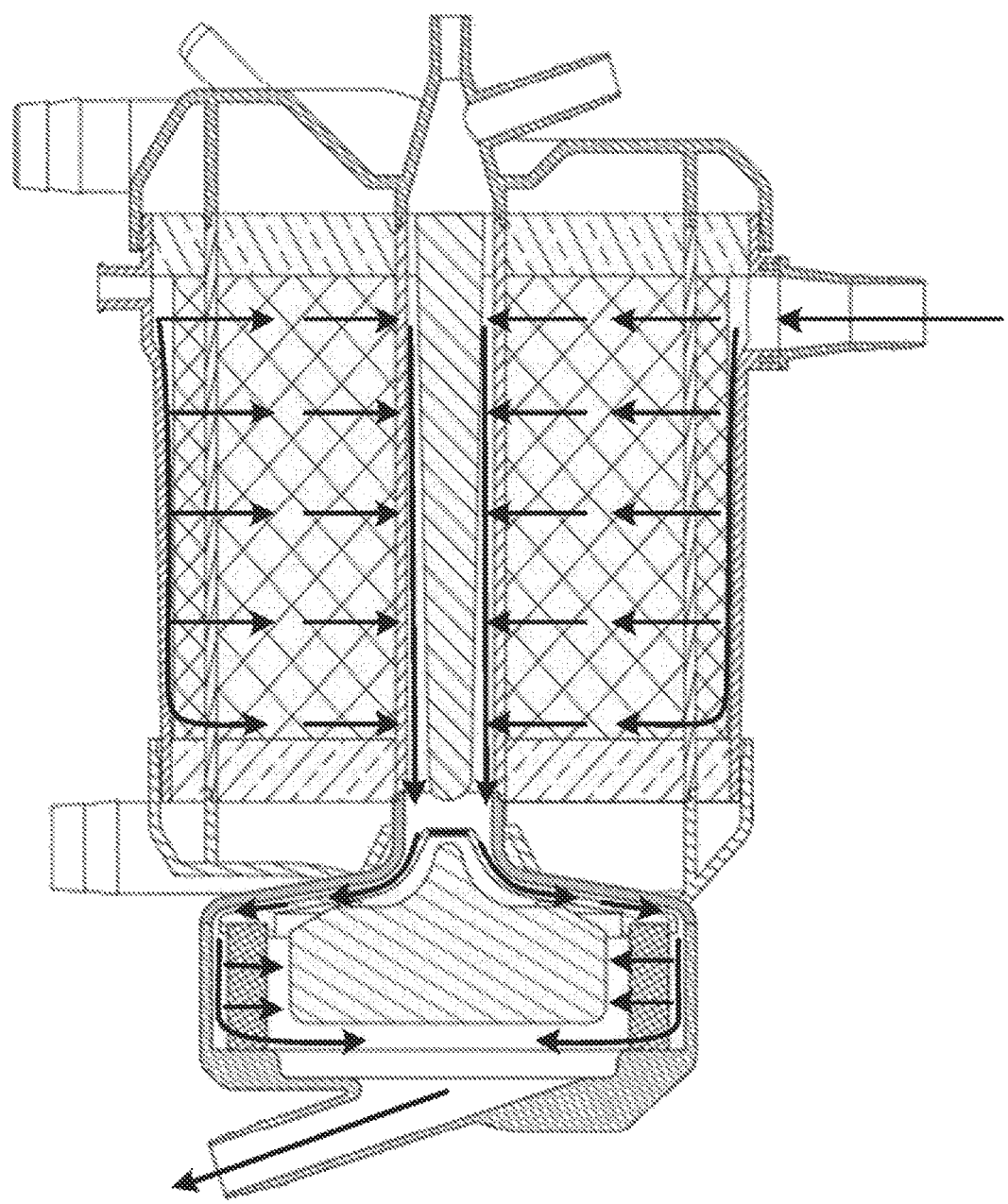
FIG. 8 is a schematic diagram of a flow direction of blood in the integrated membrane oxygenator according to some embodiments of the present disclosure.

FIG. 8 is a schematic diagram of a flow direction of blood in an integrated membrane oxygenator according to some embodiments of the present disclosure. As shown in FIG. 8, the blood may enter the oxygenator from the blood inlet 201, transversely pass through the temperature-changing membrane 403 and the oxygen pressure membrane 402, gather in a space where the mandrel 401 is located, and then enter the filter. A diversion structure of the filter may disperse and decelerate the blood. The decelerated blood may transversely pass through a filter screen, gather into the accommodation space, and then flow out from an outlet connected with the accommodation space.

The technical features of the above-described embodiments can be combined arbitrarily. For the sake of brevity, all possible combinations of the technical features in the above embodiments are not described. However, the combinations of these technical features should be regarded as the scope described in the present disclosure as long as there is no contradiction between the combinations of these technical features.

The above embodiments merely illustrate some embodiments of the present disclosure, which are described specifically and in detailed, but should not be understood as a limit on the scope of the present disclosure. It should be noted that for those skilled in the art, without departing from the concept of the present disclosure, some modifications and improvements can also be made, which all belong to the protection scope of the present disclosure. Therefore, the protection scope of the present disclosure should be subject to the appended claims.

What is claimed is:

1. An integrated membrane oxygenator, comprising an oxygenator and a filter attached to the oxygenator, wherein the oxygenator includes an upper cover, a lower cover, a shell, and an oxygenation structure, the upper cover is divided into a first blood path space, a first gas path space, and a first water path space sequentially from a center to an outer edge, the upper cover is provided with a gas inlet connected with the first gas path space, a first vent connected with the first blood path space, and a water inlet connected with the first water path space, the lower cover is divided into a second blood path space, a second gas path space, and a second water path space sequentially from a center to an outer edge, the lower cover is provided with a blood outlet connected with the second blood path space, a gas outlet connected with the second gas path space, and a water outlet connected with the second water path space, two ends of the shell are respectively connected with the upper cover and the lower cover, a blood inlet connected with an inner cavity of the shell is arranged on the shell near the upper cover, the oxygenation structure arranged in the inner cavity of the shell includes a mandrel, an oxygen pressure membrane, and a temperature-changing membrane, an upper end of the mandrel enters the first blood path space, the upper end of the mandrel is opposite to the first vent, a lower end of the mandrel is opposite to the blood outlet, the oxygen pressure membrane is arranged around the mandrel, the oxygen pressure membrane is connected with the first gas path space and the second gas path space, the temperature-changing membrane is arranged around the oxygen pressure membrane, and the temperature-changing membrane is connected with the first water path space and the second water path space; and the filter includes a filter shell, a diversion structure, and a filter screen, the diversion structure and the filter screen are arranged in a cavity of the filter shell, a lower part of the filter shell is provided with an outlet connected with the cavity of the filter shell, an upper part of the filter shell is provided with an inlet connected with the cavity of filter shell, the inlet is connected with the blood outlet, a top surface of the diversion structure is provided with a protruding part that protrudes towards the inlet, the protruding part is opposite to the lower end of the mandrel, and the filter screen is located between a bottom surface of the filter shell and the diversion structure.

2. The integrated membrane oxygenator of claim 1, wherein the diversion structure includes a core and a diversion cover, the diversion cover is arranged on the core, the filter screen is arranged on an outer periphery of the core and located between an bottom surface of the filter shell and the diversion cover, and an upper end of the diversion cover is the protruding part;

a first channel is arranged between the diversion cover and the filter shell, a second channel is arranged between the filter screen and the filter shell, and the first channel is connected with the second channel; and an accommodating space is formed among the core, the filter screen, and the bottom surface of the filter shell, and the accommodating space is connected with the outlet.

3. The integrated membrane oxygenator of claim 2, wherein the diversion cover includes a first opening, a second opening, and a transitional surface extending from the first opening to the second opening, the first opening is smaller than the second opening, the first opening is below the mandrel, and a unidirectional membrane is arranged at the first opening;

a lower part of the core is cylindrical, and an upper part of the core is tightened from an edge to a middle part;

and the upper part of the core passing through the second opening is located below the first opening, a side of the core is connected with the diversion cover, a third channel is arranged between the upper part of the core and an inner side of the diversion cover, and the third channel is connected with the accommodating space.

4. The integrated membrane oxygenator of claim 3, wherein the bottom surface of the filter shell has a protrusion arranged along an inner wall of the filter shell, a lower end of the filter screen is connected with the protrusion, and an upper end of the filter screen is connected with the diversion cover.

5. The integrated membrane oxygenator of claim 2, wherein
the upper cover is further provided with a recirculation port connected with the first vent, and the shell is provided with a second vent; and
the second vent is provided with a unidirectional breathable membrane.

6. The integrated membrane oxygenator of claim 1, wherein a gap is arranged between the temperature-changing membrane and an inner wall of the shell, and a width of the gap gradually decreases from the upper cover to the lower cover.

7. The integrated membrane oxygenator of claim 1, wherein
the oxygenator further includes a first plugging layer and a second plugging layer, the first plugging layer is arranged at a junction of the shell and the upper cover, and the second plugging layer is arranged at a junction of the shell and the lower cover;
the oxygen pressure membrane includes a plurality of ventilation pipes, and each ventilation pipe of the plurality of ventilation pipes is a hollow pipe with openings at both ends, one end of each ventilation pipe penetrates into the first plugging layer and is connected with the first gas path space, and the other end of each ventilation pipe penetrates into the second plugging layer and is connected with the second gas path space; and
the temperature-changing membrane includes a plurality of temperature-changing pipes, and each temperature-changing pipe of the plurality of temperature-changing pipes is a hollow pipe with openings at both ends, one end of each temperature-changing pipe penetrates into the first plugging layer and is connected with the first water path space, and the other end of each temperature-changing pipe penetrates into the second plugging layer and is connected with the second water path space.

8. The integrated membrane oxygenator of claim 1, wherein the integrated membrane oxygenator further includes a turbulence structure for guiding blood to flow transversely, and the turbulence structure is arranged between the shell and the temperature-changing membrane.

9. The integrated membrane oxygenator of claim 8, wherein
the turbulence structure includes a plurality of protrusions protruding from the inner wall of the shell towards the temperature-changing membrane; and the plurality of protrusions are distributed in a ladder shape, and a distance between the protrusion close to the upper cover and the temperature-changing membrane is greater than a distance between the protrusion close to the lower cover and the temperature-changing membrane.

10. The integrated membrane oxygenator of claim 1, wherein
the shell is a cylindrical shell, and an inner diameter of the shell decreases sequentially from the upper cover to the lower cover; and
a cross section of the mandrel gradually decreases from the upper cover to the lower cover.

11. The integrated membrane oxygenator of claim 1, wherein
the upper cover is provided with a first partition ring and a second partition ring, the second partition ring is arranged around the first partition ring, the first partition ring partitions the first blood path space and the first gas path space, and the second partition ring partitions the first gas path space and the first water path space; and
the lower cover is provided with a third partition ring and a fourth partition ring, the fourth partition ring is arranged around the third partition ring, the third partition ring partitions the second blood path space and the second gas path space, and the fourth partition ring partitions the second gas path space and the second water path space.

* * * * *